United States Patent [19]

Witzel et al.

[11] Patent Number: 4,999,436

[45] Date of Patent: Mar. 12, 1991

[54] ARYL-SUBSTITUTED THIOPHENE 3-OLS, DERIVATIVES AND ANALOGS USEFUL AS LIPOXGENASE INHIBITORS

[75] Inventors: Bruce E. Witzel, Westfield; Debra L. Allison, Basking Ridge; Charles G. Caldwell, Scotch Plains; Kathleen Rupprecht, Cranford, all of N.J.

[73] Assignee: Merck & Co., Inc., Rahway, N.J.

[21] Appl. No.: 397,325

[22] Filed: Aug. 22, 1989

Related U.S. Application Data

[63] Continuation of Ser. No. 222,358, Jul. 20, 1988, abandoned, which is a continuation of Ser. No. 99,586, Sep. 22, 1987, abandoned.

[51] Int. Cl.$^5$ .............................................. C07D 333/74
[52] U.S. Cl. .................................... 549/45; 549/52; 549/55; 546/274; 548/525
[58] Field of Search .......................... 549/45, 52, 55; 548/525; 546/274

[56] References Cited

U.S. PATENT DOCUMENTS

| | | | |
|---|---|---|---|
| 3,644,399 | 2/1972 | Brown et al. | 548/562 |
| 3,655,692 | 4/1972 | Tsung-Ying et al. | 549/68 |
| 3,892,774 | 7/1975 | Ebnother et al. | 549/52 |
| 3,929,833 | 12/1975 | Krieger et al. | 549/64 |
| 4,174,405 | 11/1979 | Relyea et al. | 549/66 |
| 4,381,311 | 4/1983 | Haber | 549/75 X |
| 4,432,974 | 2/1984 | Haber | 546/14 X |
| 4,500,520 | 2/1985 | Haber | 514/63 |
| 4,645,777 | 2/1987 | Burkart et al. | 514/444 |
| 4,645,842 | 2/1987 | Corey | 549/62 |
| 4,663,344 | 5/1987 | Durette et al. | 549/56 |
| 4,704,460 | 12/1987 | Corey | 549/66 |

FOREIGN PATENT DOCUMENTS

| | | |
|---|---|---|
| 39270 | 3/1970 | Belgium . |
| 0154887 | 9/1985 | European Pat. Off. . |
| 2724494A1 | 5/1977 | Fed. Rep. of Germany . |
| 2353228 | 12/1977 | France . |

OTHER PUBLICATIONS

Shen et al., "The Development of Antiasthmatic Drugs", Part III, ed. D. R. Buckle et al. Butterworth Publishers, Kent England 1983, pp. 315–317 and 331–334.
Hortough, Thiophene and Derivatives, (1952), p. 472.
Fiesselman, et al., Unknown Journal, vol. 89, Nov. 8, 1956.
K. Buggle, et al. J. C. S. Perkin I. pp. 2630–2634 (1972).
B. Hedegaard, et al., Tetrahedron, vol. 77 pp. 3853 to 3859, (1971). Wilkerson, et al., Pharm. Res. and Dev. Div., DuPont and Company, Wilmington, Del. (1985).
Myers et al., Pharm. Res. and Dev. Div., DuPont and Co., Wilmington, Del. (1985).
D. R. Robinson et al., J. Exp. Med, vol. 163, 1986, pp. 1509–1517.
B. Samuelsson, Science, vol 220 pp. 568–575, (1983).
D. M. Bailey Annual Repts in Med. Chem., pp. 203–217, (1982).
Tesfay, B. et al., J. C. S. Perkins I, pp. 1147–1150 (1978).
Tesfay B. et al., J. C. S. Perkin I, pp. 2276–2281 (1979).
Hartough, Chem of Heterocyclic Compounds (1952) pp. 52–54.
Chem. Abst., Parnes, vol. 90, (1979) 87166p.
Chem. Abst., Kalantar, vol. 58 (1963) 11146b.

*Primary Examiner*—Mary C. Lee
*Assistant Examiner*—Jacqueline Haley
*Attorney, Agent, or Firm*—Frank P. Grassler; Roy D. Meredith; Hesna J. Pfeiffer

[57] ABSTRACT

Aryl substituted thiophenes 3-ols, its dihydro derivatives, 1-oxide and 1,1-dioxide analogs, as well as aryl substituted furans, are 5-lipoxygenase inhibitors useful in the treatment of inflammation and other leukotriene-mediated diseases.

4 Claims, No Drawings

ARYL-SUBSTITUTED THIOPHENE 3-OLS, DERIVATIVES AND ANALOGS USEFUL AS LIPOXGENASE INHIBITORS this is a continuation, of application Ser. No. 222,358 filed 7/20/88, now abandoned, which is a continuation of application Ser. No. 099,586 filed Sept. 22, 1987, now abandoned.

BACKGROUND OF THE DISCLOSURE

This invention relates to aryl-substituted thiophene 3-ols, its dihydro derivatives, 1-oxide and 1,1-dioxide analogs, as well as aryl substituted furans, alal having the general formula:

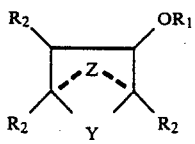

wherein Z represents the number of double bonds and is 1 or 2; Y is S, SO, $SO_2$ or O; $R_1$ forms an alcohol derivative or ester, acetal, carbonate, carbamate, aralkyl or acetol group; and $R_2$ is H, alkyl, or aryl.

The compounds of this invention are 5-lipoxygenase inhibitors and are useful in the treatment of inflammation and other leukotriene-mediated diseases.

Among various potent biological mediators derived from the oxygenation of arachidonic acid, compounds characterized as prostaglandins or leukotrienes have been linked to various diseases. Notably, the biosynthesis of prostaglandins has been identified as a cause of inflammation, arthritic conditions (e.g., rheumatoid arthritis, osteoarthritis and gout), psoriasis, inflammatory bowel disease, and pain. Furthermore, the formation of leukotrienes has been connected to immediate hypersensitivity reactions and proinflammatory effects. It has been established that arachidonic acid undergoes oxygenation via two major enzymatic pathways:

(1) The pathway catalyzed by the enzyme cyclooxygenase; and
(2) The pathway catalyzed by the enzyme 5-lipoxygenase.

Interruption of these pathways by enzyme inhibition has been explored for effective therapy. For example, non-steroidal anti-inflammatory drugs (NSAID) such as aspirin, indomethacin and diflunisal are known cyclooxygenase inhibitors which inhibit the process wherein arachidonic acid is oxygenated via cyclooxygenase to prostaglandins and thromboxanes.

Recently, it has been observed that certain leukotrienes are responsible for diseases related to immediate hypersensitivity reactions such as human asthma, allergic disorders, and skin diseases. In addition, certain leukotrienes and derivatives thereof play an important role in causing inflammation (B. Samuelson, *Science*, 220, 568 (1983); D. Bailey et al, *Ann. Rpts. Med. Chem.*, 17, 203 (1982))

For example, acute systemic anaphylaxis and other immediate hypersensitivity reactions are accompanied by the release of several mediators, including three leukotrienes, $LTC_4$, $LTD_4$ and $LTE_4$. These three leukotrienes have the properties of inducing bronchoconstriction and alteration in vascular permeability. A fourth leukotriene, $LTB_4$, has potent effects on chemotoxis and adherence of leukocytes. All four of these leukotrienes are produced by action of the enzyme 5-lipoxygenase on arachidonic acid. See, e.g. D. R. Robinson et al., *J. Exp. Med.* 163, 1509 (1986).

Through recent research, 5-lipoxygenase inhibitors have also been linked to the treatment of eye inflammation and used as cytoprotective agents.

To be an effective and acceptable topical agent for treating eye inflammation, a drug must not only penetrate the ophthalmic tissues to reach the active sites within the eye, but it must also be devoid of those side effects including irritation, allergic reaction and the like, which are contra-indications to long term administration.

With respect to the cytoprotective activity, it has been known that (1) gastric cytoprotection does not involve inhibition of gastric acid secretion. For example, prostaglandin F2B does not inhibit gastric acid secretion, but it does induce gastric cytoprotection (S. Szabo et al., *Experimentia*, 38, 254, 1982); (2) lower effective dosages of cyto-protective agents are required than that of gastric acid inhibitors; and (3) the cytoprotective activity of a compound may be observed in both animals and man by noting the increased resistance of gastrointestinal mucosa to strong irritants. For example, animal studies have shown that cytoprotective compounds will prevent gastric lesions induced by oral administration of strong acids, strong bases, ethanol, hypertonic saline, etc.

BRIEF DESCRIPTION OF THE INVENTION

Novel inhibitors of lipoxygenase, of the general formula are disclosed:

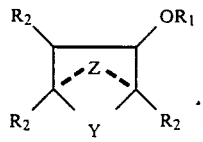

or physiologically acceptable salts thereof, wherein Z represents the number of double bonds in the 5 membered ring and Z is 1 or 2; and
Y is S, SO, $SO_2$ or O;
$R_1$ is H, acyl, aroyl, carbonate, carbamoyl, alkoxyalkyl, or alkylthioalkyl;
$R_2$ is H, phenyl, substituted phenyl, heteroaryl, substituted heteroaryl, aralkyl, alkyl, alkoxy, haloalkyl, halo, aminoalkyl, alkylaminoalkyl, alkoxyalkyl, hydroxyalkyl, amino, nitro, cyano, acyl, aroyl, acylalkyl, alkylthio, alkylsulfinyl, alkylsulfonyl, bridged methylene, alkylthioalkyl, alkylsulfinylalkyl, alkylsulf-onylalkyl, arylthio, arylsulfonyl, arylsulfonyl, or cycloalkyl; wherein at least one $R_2$ group must be an aryl or heteroaryl.
and $R_2$ at any given position is the same or different as $R_2$ at any other position.

The compounds are useful in the treatment of inflammation, pain and fever associated with inflammation, arthritic conditions, asthma, allergic disorders such as allergic rhinitis and chronic bronchitis, skin diseases like psoriasis and atopic eczema, cardiovascular or vascular disorders, and other diseases involving leukotrienes.

ABBREVIATIONS AND DEFINITIONS $Ac_2O$ = acetic anhydride
aq. = aqueous

DBU=1,8-diazobicyclo [5.4.0] undec-5-ene
DDQ=2,3-dichloro 5,6-dicyano-1,4-benzoquinone
4-DMAP=4 dimethylaminopyridine
Pyr=pyridine
t-BuOK=potassium tert-butoxide
THF=tetrahydrofuran

DETAILED DESCRIPTION OF THE INVENTION

A. Scope of Products

The compounds of the present invention specifically encompass lipoxygenase inhibitors of the formula:

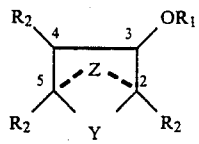  I or physiologically acceptable salts thereof, wherein Z represents the number of double bonds in the 5-membered ring and $Z=1$ or 2. Y is S, SO, $SO_2$ or O. Thus the dihydro analogs of thiophene and furan are included.
$R_1$ is
(a) H;
(b)

wherein $R_3$ is loweralkyl, especially $C_{1-6}$ alkyl such as methyl, ethyl, i-propyl, n-propyl, t-butyl, n-butyl, i-pentyl, n-pentyl or n-hexyl; $R^3$ may also be aryloxy, lower alkoxy, lower alkyl thio, monoloweralkylamino, diloweralkylamino, alkoxyalkyl, or carbo lower alkoxy lower alkyl;
(c)

wherein $R_4$ is aryl, especially $C_{-14}$ aryl, e.g., naphthyl, anthryl, phenyl or substituted phenyl of formula

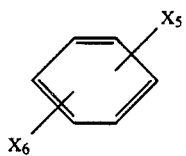

wherein $X_5$ and $X_6$ independently are:
(1) Q, where Q is H, loweralkyl especially $C_{1-6}$ alkyl, haloloweralkyl especially fluoro or chloro $C_{1-6}$ alkyl such as trifluoromethyl, phenyl or substituted phenyl, or naphthyl;
(2) halo especially chloro, fluoro, bromo or iodo;
(3) loweralkenyl especially $C_{2-6}$ alkenyl such as ethenyl and allyl;
(4) loweralkynyl especially $C_{2-6}$ alkynyl, for example, ethynyl or n-butynyl;
(5) —SQ;
(6) —OQ;
(7) —CHQCOQ$^1$, where $Q^1$ is any species of Q and can be the same as or different from Q;
(8) —CHQCOOQ$^1$;
(10) —CH$_2$SQ or —CHSQ$^1$;
(11) —CH$_2$OQ or —CHQOQ$^1$;
(12) —COQ;
(13) —COOQ;
(14) —OCOQ;
(15) —NQQ$^1$;
(16) —NQCOQ$^1$;
(17) —NQ(OQ$^1$);
(18) —NQ(SQ$^1$);
(19) —NQSO$_2$Q$^1$;
(20) —SO$_2$NQQ$^1$;
(21) —SOQ;
(22) —SO$_2$Q;
(23) —SO$_3$Q;
(24) —CN;
(25) —NO$_2$;
(26) —CONQQ$^1$;
(27) —NO;
(28) —CSQ;
(29) —CSNQQ$^1$;
(30) —CF$_2$SQ;
(31) —CF$_2$OQ;
(32) —NQCONHQ$^1$ or NQCONQ$^1$Q$^2$ wherein $Q^2$ is any species of Q and $Q^1$ is any species of Q, and $Q^2$ can be the same as or different from $Q^1$;

(d) 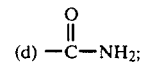

(e) —R$_3$—O—R$_3$;
(f) —R$_3$—S—R$_3$; or
(g) QOQ$^1$; and
$R_2$ is
(a) H;
(b) $R_2$;
(c) lowercycloalkyl especially $C_{3-6}$ cycloalkyl, e.g., cyclopropyl, cyclopentyl and cyclohexyl;
(d) halo;
(e) haloloweralkyl especially halo $C_{1-6}$ alkyl, e.g. $CF_3$—, $CHF_2$—, $C_2F_5$—;
(f) heteroaryl or heteroaryl substituted with $X_5$ and $X_6$ especially pyridyl, pyrryl, furyl or thienyl wherein $X_5$ and $X_6$ are as previously defined;
(g) benzyl or substituted benzyl of formula

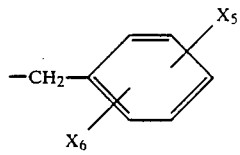

wherein $X_5$ and $X_6$ are as previously defined;
(h) loweralkynyl especially $C_{1-6}$ alkynyl such as —C≡CH; $CH_3$—C≡C—, or HC≡C—$CH_2$—;
(i) loweralkenyl especially $C_{1-6}$ alkenyl, such as $CH_2$=CH—, $CH_3CH$=CH—, $CH_2$=$CHCH_2$—, $CH_3CH$=CH—$CH_2$— or $(CH_3)_2C$=CH;
(j) —R$_3$;
(k) —O—R$_3$;
(l) —NHR$_3$;

(m) —T¹—NH—T², wherein T¹ is any species of R₃ and T² is any species of R₃ and T¹ is the same or different from T²;
(n) —T¹OT²;
(o) —R₃OH;
(p) —NH₂;
(g) —NO₂;
(r) —CN;

(s) 

(t) 

(u) —SR₃;
(v) —SR₃;

(w) 

(x) —T¹—S—T²;

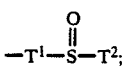

(z) —T¹—SO₂—T²;
(aa) —S—R₄;

(ab) 

(ac) —SO₂—R₄;
(ad) phenylloweralkenyl of formula

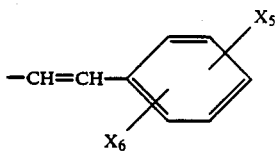

where X₅ and X₆ are as previously defined;
(ae) phenylloweralkynyl of formula

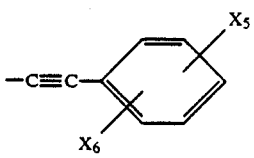

where X₅ and X₆ are as previously defined;

(af)  wherein R⁵ is R₁;

(ag) 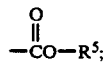

(ah) 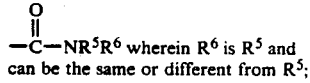 wherein R⁶ is R⁵ and can be the same or different from R⁵;

-continued (ai) 

(aj) 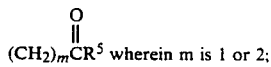 wherein m is 1 or 2;

(ak) 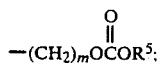

(al) —(CH₂)ₘNR⁵R⁶; or (am) 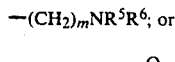 and

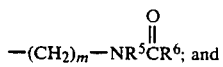

R₂ may form a bridged methylene of between 3 and 10 carbon atoms with an adjacent R₂ group;

at least one R₂ group of Formula I is either R₄ or heteroaryl or heteroaryl substituted with X₅ and X₆ especially pyridyl, pyrryl, furyl, or thienyl wherein X₅ and X₆ are as previously defined; and each R₂ group may be the same or different from another R₂ group on the same molecule;

(y) with the proviso that R₂ at the 2-position is neither

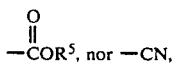

when Y is X, Z is 2 and R₁ is H; with the additional proviso that R₂ is the 5-position is not methyl when Y is S, Z is 2, R₁ is H, and R₂ at the 2-position is phenyl.

Most preferably, the compounds of the present invention are chemical products of the formula:

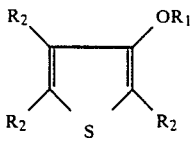

wherein
R₁ is H, loweralkoxy loweralkyl, or

when R₃ is loweralkyl, especially C₁₋₆ alkyl such as methyl, ethyl, i-propyl, n-propyl, t-butyl, n-butyl, i-pentyl, n-pentyl or n-hexyl; R₃ may also be loweralkoxy loweralkyl;

R₂ is aryl at the 2 position of thiophene or the 5-position thereof, or both;

or physiologically acceptable salts thereof.

B. Synthetic Routes of the Compounds

The novel thiophene derivatives of the present invention can be prepared by the steps of (a) a Michael addition of a carbanion such as R-S⁻ to an α,β-unsaturated acid derivative; followed by (b) ring closure to form a five membered ring; and (c) oxidation, if needed.

These protocols were derived in part from Reinhoudt, D. N. et al., *Synthesis* 39, 368 (1978); Buggle, K. et al., *J.C.S. I*, 2630 (1972); Hedegaard, B. et al., *Tetra-*

*hedron* 27, 3853 (1971); and Scheibler, V. H. et al., *J. Prakt. Chem.* 2, 127 (1955).

Schematically, this route can generally be represented by the following:

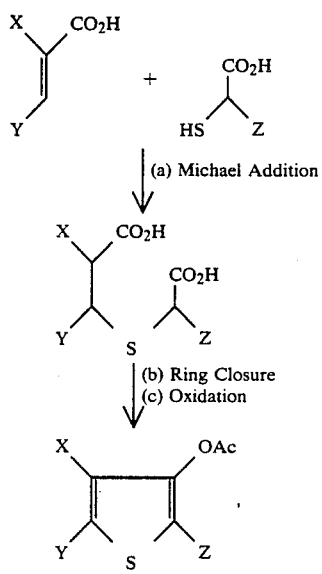

wherein X, Y and Z are each the same or different, and are each species of $R_2$, as defined above.

Alternatively, a triple-bonded reactant can be used instead of a double-bonded unsaturated compound, i.e.,

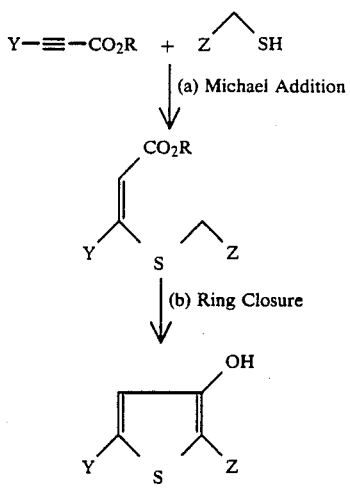

Michael Additions are typically carried out according to Organic Reactions 10, 182 (1959).

Typical solvents useful for the ring closure reaction include, but are not limited to, $Ac_2O$, Pyr, THF, $Et_3N$, or $CH_3CN$. Catalysts include NaOAc or t-BuOK. DDQ can be used in ring dehydrogenation. For acetylations, 4-DMAP is a catalyst of choice.

Formation of thiophenes of this invention may also be performed by the methods derived in part from Fiesselmann, H. et al., *Ber* 1907 (1956). By these methods ring closure is performed on an aryl or diaryl, δ-di-(alkylestermercapto)butyric acid ester, i.e.

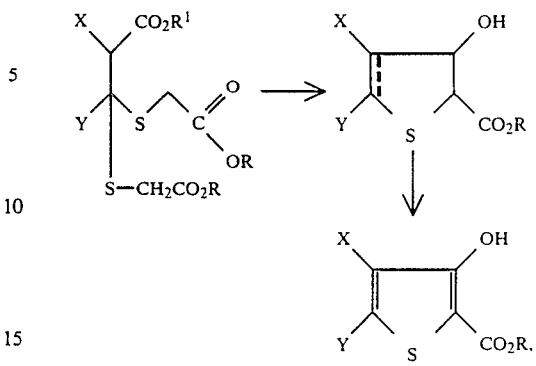

wherein X and Y are each separately selected from the group consisting essentially of aryl, alkyl, aralkyl or carboxyalkyl. Decarboxylation of the 2-acid, with or without use of a hydroxy protecting group, yields the desired aryl or diaryl thiophene-3ol.

Alternatively, one-step condensation reactions can be carried out via a novel modification of the thiophenedicarboxylate synthesis of Hinsberg, T. Ber. 43, 901 (1910). For example,

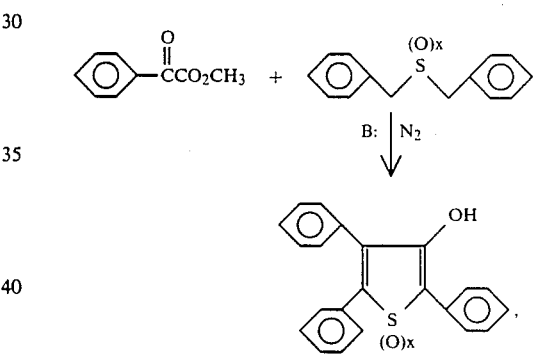

wherein X is 0, 1 or 2. This type of procedure has the advantage of reducing the number of steps for laboratory or commercial synthesis.

The corresponding sulfones and sulfoxides may be synthesized, despite low yields, by direct oxidation of the corresponding aryl substituted thiophene. The peroxy acid method is generally preferable. Better yields are obtained when the intermediate Michael adduct is first oxidized at the sulfur to the desired oxidation state, then ring closed.

Saturated, cyclic, 4,5-disubstituted 3-acetoxy-2-arylthiophenes may be prepared by base mediated ring closure of the dithioketal.

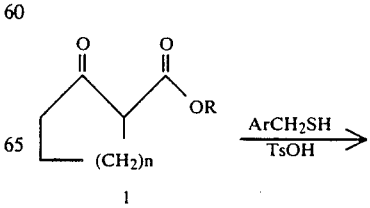

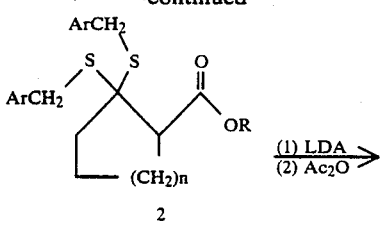

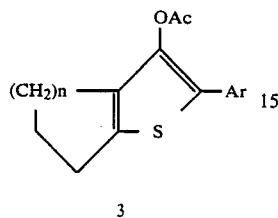

Treatment of 2-carboethoxycycloalkanone (1) with the appropriate thiol under dehydrating conditions with acid catalysis affords the dithioketal (2), which is then deprotonated with a strong base [e.g. lithium diisopropylamide (LDA), NaH, Potassium t-butoxide] to effect cyclization (3). The 3-hydroxy group may be converted to the acetate by addition of acetic anhydride to the reaction mixture or may be isolated directly.

Analogs of the 3-acetoxy-2,5 diarylthiophenes in which the 5-aryl substituent is bridged to the 4-position of the thiophene by a hydrocarbon bridge may be prepared in a similar manner from the corresponding 2-carbomethoxyarylcycloalkanone.

In these cases, for example, carbomethoxybenzocycloalkanone (4) is converted to the enolphosphate by treatment with a diaryl chlorophosphate and base (e.g. triethylamine, potassium t-butoxide, NaH) in a solvent such as tetrahydrofuran or N,N'-dimethyl-formamide and the enol-phosphate is replaced by Michael addition-/elimination with the appropriate arylmethyl mercaptan and base (e.g. triethylamine, potassium t-butoxide, NaH) in the same solvent, to yield compound 5. Deprotonation with a strong base cyclizes, yielding 6.

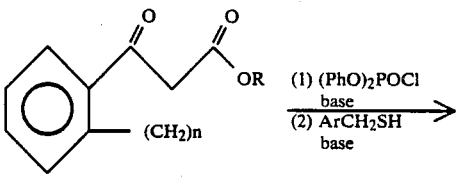

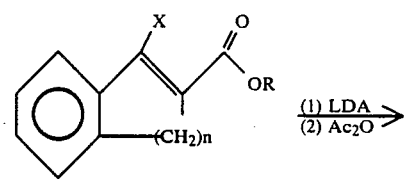

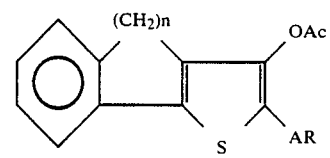

Additional reaction schemes can be derived from Gronowitz, S. (ed.), *Thiophene and Its Derivatives*, I John Wiley and Sons, 1985, passim.

C. Utility of the Compounds Within the Scope of the Invention

This invention also relates to a method of treatment for patients (or mammalian animals raised in the dairy, meat, or fur industries or as pets) suffering from disorders or diseases mediated by prostalandins and/or leukotrienes, and gastric irritation or lesion. More specifically, this invention is directed to a method of treatment involving the administration of one or more of the enzyme inhibitors of formula (I) as the active constituent.

Accordingly, a compound of Formula (I) can be used among other things to reduce pain and inflammation, to correct respiratory, cardiovascular, and intravascular alterations or disorders, and to regulate immediate hypersensitivity reactions that cause human asthma and allergic conditions.

For the treatment of inflammation, arthritis conditions, cardiovascular disorders, allergy, psoriasis, asthma, or other diseases mediated by prostaglandins and/or leukotrienes, a compound of Formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intravascular injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, agueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or algenic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The agueous suspensions may also contain one or more preservatives, for example ethyl, or n-propyl, p hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid. Dispersible powders and granules suitable for preparation of an agueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin, or mixtures of these. Suitable emulsifying agents may be naturally-occurring gums, for example gum acacia or gum tragacanth, naturally occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable agueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3 butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic monoor diglycerides. In addition, fatty acids such as oleic acid find use in the preparation of injectables.

The compounds of Formula (I) may also be administered in the form of suppositories for rectal administration of the drug These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula (I) are employed.

Dosage levels of the order of from about 0.01 mg to about 150 mg per kilogram of body weight per day are useful in the treatment of the above-indicated conditions (about 0.5 mg to about 7.5 gms. per patient per day). For example, inflammation may be effectively treated by the administration of from about 0.2 to 50 mg of the compound per kilogram of body weight per day (about 20 mg to about 3.5 gms per patient per day). Preferably a dosage of from about 1 mg to about 20 mg per kilogram of body weight per day may produce good results (about 25 mg to about 1 gm per patient per day).

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain between from about 1 mg to about 500 mg of an active ingredient.

Particularly, for use in treatment of ophthalmic conditions including those associated with elevated intraocular pressure such as glaucoma or other inflammation in the eye. The active compound can be administered topically or systemically when it is appropriate. The dose administered can be from as little as 0.1 to 25 mg or more per day, singly, or preferably on a 2 to 4 dose per day regimen although a single dose per day is satisfactory.

When given systemically, the drug can be given by any route, although the oral route is preferred. In oral administration the drug can be employed in any of the usual dosage forms such as tablets or capsules, either in a contemporaneous delivery or sustained release form. Any number of the usual excipients or tableting aids can likewise be included.

When given by the topical route, the active drug or an ophthalmologically acceptable salt thereof such as the sodium or potassium salt is formulated into an ophthalmic preparation. In such formulations, from 0.1% to 15% by weight can be employed. The objective is to administer a dose of from 0.1 to 10 mg per eye per day to the patient, with treatment continuing so long as the condition persists.

Thus, in an ophthalmic solution, insert, ointment or suspension for topical delivery, or a tablet, intramuscular, or intravenous composition for systemic delivery, the active medicament or an equivalent amount of a salt thereof is employed, the remainder being carrier, excipients, preservatives and the like as are customarily used in such compositions.

The active drugs of this invention are most suitably administered in the form of ophthalmic pharmaceutical compositions adapted for topical administration to the eye such as a suspension, ointment, or as a solid insert. Formulations of these compounds may contain from 0.01 to 15% and especially 0.5% to 2% of medicament. Higher dosages as, for example about 10%, or lower dosages can be employed provided the dose is effective in reducing or controlling elevated intraocular pressure. As a unit dosage from between 0.001 to 10.0 mg, preferably 0.005 to 2.0 mg, and especially 0.1 to 1.0 mg of the compound is generally applied to the human eye, generally on a daily basis in single or divided doses so long as the condition being treated exists.

As with all medications, dosage requirements are variable and must be individualized on the basis of the disease and the response of the patient.

The pharmaceutical preparation which contains the active compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The pharmaceutical preparation may also be in the form of a solid insert such as one which after dispensing the drug remains essentially intact, or a bio-erodible insert that either is soluble in lacrimal fluids, or otherwise disintegrates.

The following examples of ophthalmic formulations are given by way of illustration.

EXAMPLE A

| A compound of Formula (I) | 1 mg. | 15 mg. |
|---|---|---|
| Monobasic sodium phosphate .2H$_2$O | 10 mg. | 5 mg. |
| Dibasic sodium phosphate .12H$_2$O | 30 mg. | 15 mg. |
| Benzalkonium chloride | 0.1 mg. | 0.1 mg. |
| Water for injection q.s. ad. | 1.0 ml. | 1.0 ml. |

Compound A, phosphate buffer salts, and benzalkonium chloride are added to and dissolved in water. The pH of the composition is adjusted to 6.8 and diluted to volume. The composition is rendered sterile by ionizing radiation.

EXAMPLE B

| A Compound of formula (I) | 5 mg. |
|---|---|
| petrolatum q.s. ad. | 1 gram |

The active compound and the petrolatum are aseptically combined.

EXAMPLE C

| A Compound of formula (I) | 1 mg. |
|---|---|
| Hydroxypropylcellulose q.s. | 12 mg. |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R. H. at 30° C.) for two to four days. After removal from the humidity cabinet, the vials are stoppered and then capped. The vials containing the hydrate insert are then autoclaved at 250° F. for ½ hour.

EXAMPLE D

| A Compound of formula (I) | 1 mg. |
|---|---|
| Hydroxypropyl cellulose q.s. ad. | 12 mg. |

Ophthalmic inserts are manufactured from a solvent cast film prepared by making a viscous solution of the powdered ingredients listed above using methanol as the solvent. The solution is placed on a Teflon plate and allowed to dry at ambient conditions. After drying, the film is placed in an 88% R. H. cabinet until it is pliable. Appropriately sized inserts are cut from the film.

EXAMPLE E

| A Compound of formula (I) | 1 mg. |
|---|---|

-continued

| Hydroxypropylmethyl cellulose q.s. ad. | 12 mg. |

Ophthalmic inserts are manufactured from a solvent cast film which is prepared by making a viscous solution of the powdered blend of the above ingredients using a methanol/water solvent system (10 ml. methanol is added to 2.5 g. of the powdered blend, to which 11 ml. of water (in three divided portions) is added. The solution is placed on a Teflon plate and allowed to dry at ambient conditions. After drying, the film is placed in an 88% R. H. cabinet until it is pliable. Appropriately sized inserts ar then cut from the film.

EXAMPLE F

| A Compound of formula (I) | 1 mg. |
| Hydroxypropylmethyl cellulose q.s. ad. | 12 mg. |

Ophthalmic inserts are manufactured from compression molded films which are prepared on a Carver Press by subjecting the powdered mixture of the above ingredients to a compressional force of 12,000 lbs. (gauge) at 350° F. for one minute. The film is cooled under pressure by having cold water circulate in the platen. Ophthalmic inserts are then individually cut from the film with a punch. Each insert is placed into a vial, which is then placed in a humidity cabinet (88% R. H. at 30° C.) for two to four days. After removal from the humidity cabinet, the vials are stoppered and then capped. The vials containing the hydrated insert are then autoclaved at 250° F. for one-half hour.

It is highly preferred that the solid inserts of this invention are available for use by the patient in a pathogen free condition. Thus, it is preferred to sterilize the inserts and to insure against recontamination, the sterilization is preferably conducted after packaging. The best mode of sterilizing is to employ ionizing radiation including radiation emanating from Cobalt 60 or high energy electron beams.

EXAMPLE G

The following materials are admixed in a 1250 ml bottle: 24 g of an active compound of formula (I) which is a sufficient amount of medicament to result in a concentration of 10 mg per ml in the final samples, allowing for previously established 3.0% average; 0.4 g sodium bisulfite, 12 g NaCl, and 28 ml water (at 180° F.). This mixture, (I), is autoclaved for 30 minutes at 121° C. under 15 psi. Separately, 3 g of hydroxyethylcellulose in 720 ml of water (II) and 0.4 g of lecithin in 80 ml of water (III) were autoclaved for 30 minutes at 121° C. Then, (III) is admixed with (I) for 2 hours, and the resultant mixture poured into (II). Another mixture (IV) is prepared from 20 g of sorbitol, 2.36 ml of benzalkonium chloride, 10 g of disodium acetate, and water to give a final solution volume of 900 ml. Then, (IV) is added to the mixture of (I), (II), and (III) in sufficient quantity to give 1.8 liter overall. The 1.8 liter mixture of I, II, III, and IV is then taken and homogenized using a homogenizer at 2000 psi. Stock solutions are then prepared for polyoxyethylene (20) sorbitan monooleate by dissolving 3 g of the material in 100 ml of water, and of benzyl alcohol/β-phenyl-ethyl alcohol by admixing 50 ml of each alcohol. Varying quantities of the two stock solutions are then added to four 90 ml aliquots of the homogenized mixture of (I), (II), (III), and (IV) prepared as described above, together with sufficient water to give a total of 100 ml for each of four different samples.

Other formulations, in an oil vehicle and an ointment are exemplified in the following examples.

EXAMPLE H

Solution Composition

| A compound of formula (I) | 0.1 mg. |
| Peanut oil q.s. ad. | 0.10 mg. |

The solution is rendered sterile by filtration through a sterilizing filter.

EXAMPLE J

| A compound of formula (I) | 0.5 gm. |
| Petrolatum q.s. ad. | 1 gram |

The compound and the petrolatum are aseptically combined.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

In this invention, "lower alkyl" is defined as a saturated hydrocarbon radical with a backbone of 1-10 carbon atoms, preferably 1-6 carbon atoms Especially included are methyl, ethyl, i-propyl, n-propyl, t-butyl, n-butyl, i pentyl, n-pentyl and n-hexyl.

Aryl encompasses aromatic radicals of 6-20 carbon atoms, preferably aromatic radicals of 6-14 carbon atoms, e.g. naphthyl, anthryl, phenyl or substituted phenyl.

The following examples are provided for the purpose of illustrating the invention without limiting the scope, variation or extent of the invented subject matter.

EXAMPLE 1

3-Acetoxy-2-phenyl-5-(2-thienyl)thiophene (I)

Step A: 3-thia-2-phenyl-4-(2-thienyl)-glutaric acid (II)

To a stirred suspension of 3-(2-thienyl)acrylic acid (3.6 g, 0.023 mmol), α-mercaptophenylacetic acid [3.9 g, 0.023 mmol (J. Org. Chem. 33 1831 1968)]. and dry dioxane (15 ml) was added dropwise at room temperature and under a nitrogen atmosphere a solution of triethylamine (5.0 ml, 0.036 mmol) in dioxane (5 ml). The warming mixture was then set in an oil bath at 110° C., and kept at 110°-115° C. for ca. 40 hours. The cooled solution was then added in portions to a stirred ether-ice-water mixture containing 2N HCl (25 ml.) and this mixture allowed to reach room temperature. After separation of the layers, the ether solution was washed 2 times with water and dried over sodium sulfate. The filtered and concentrated mixture was then triturated with a small amount of ether and then brought to turbidity with hexane. After aging, the mixture was filtered from a small amount of solid, concentrated to crude oily (II) (6.4 g) and used in the following step.

Step B: 3-Acetoxy-2-phenyl-5-(2-thienyl)-dihydrothiophene (III)

A stirred, nitrogen-covered mixture of (II) (1.2 g, 0.003+mmol), anhydrous sodium acetate (0.4 g, 0.0049 mmol), and acetic anhydride (11 ml) was slowly heated to reflux (bath temperature ca. 150° C.), kept ca. 5 hours at this temperature, and allowed to cool. After removal of the volatiles (hi-vac), the residue was distributed between ether and water, the ether layer was washed 2 times with dilute sodium hydrogen carbonate solution, 1 time with water, dried (sodium sulfate), concentrated to 1.1 g crude (III), and used immediately in the next step.

Step C: 3-Acetoxy-2-phenyl-5-(2-thienyl)-thiophene (I)

To a stirred solution of crude (III) in benzene (35 ml) at room temperature was added 2,3-dichloro-5,6-dicyano-1,4-benzoguinone (1.0 g, 0.0048 mmol) all at once, and the mixture was allowed to stir overnight at ambient temperatures. The mixture was then filtered, the volatiles removed (hi-vac), and the residue chromatographed on silica gel (methylene chloride/hexane) to yield 0.35 g of the title compound. M.S. (M+)=300; NMR: consistent.

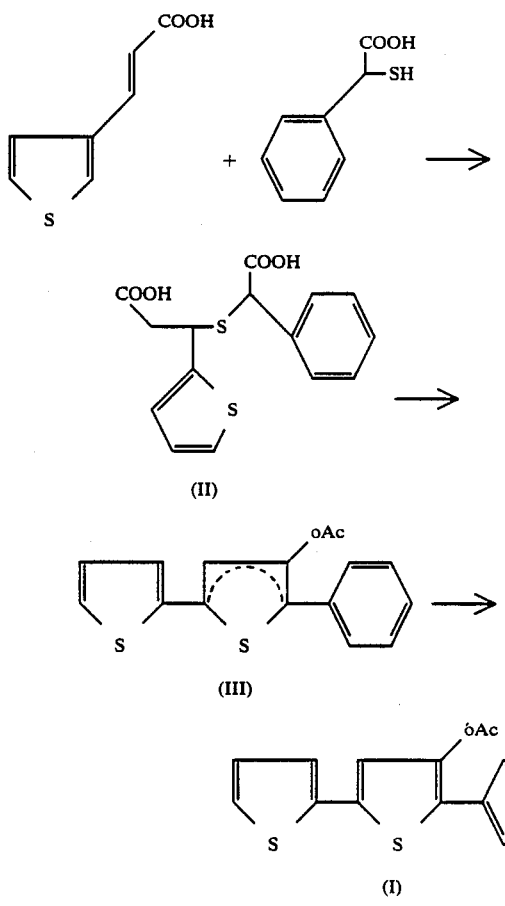

EXAMPLE 2

3-(3-(Carbomethoxy)propionyloxy)-2,5-diphenylthiophene (I)

To a stirred, ice-cooled solution of 2,5-diphenyl-3-hydroxythiophene (0.12 g, 0.5 mmol) in dried pyridine (5.0 ml) under a nitrogen atmosphere was added 3-carbomethoxypropionyl chloride (0.1 g, 0.66 mmol) over ca. 20 seconds. The mixture was allowed to stir cold for 15 minutes and then at ambient temperatures for 4 hours. The mixture was added in portions to a stirred mixture of ether, ice, water, and 2N hydrochloric acid (40 ml), the ether layer washed 2 times with water, dried over sodium sulfate, filtered and concentrated to 0.18 g of oily (I). M.S.: M+=366; NMR: consistent.

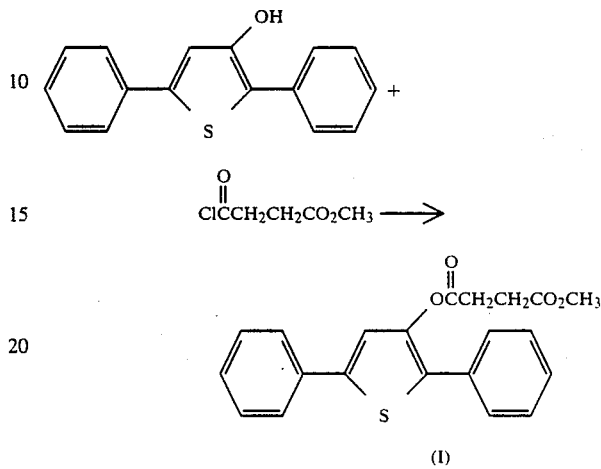

EXAMPLE 3

2,5-Diphenyl-3-(methoxymethoxy)-thiophene (II)

To a stirred, ice cooled solution of 2,5-diphenyl-3-hydroxythiophene (0.12 g, 0.5 mmol) in dried N,N-dimethylformamide (2 ml) was added sodium hydride (30 mg of a 60% suspension in mineral oil). When the initial vigorous reaction subsides (ca. 4 minutes), the mixture was allowed to stir at ambient temperatures for 20 minutes and then recooled. Chloromethyl methyl ether (0.055 ml, 0.7 mmol) was then added all at once. After stirring cold for ca. 30 minutes, the mixture was allowed to stir at ambient temperatures for ca. 4 hours and then added to a stirred ether/water mixture. The ether layer was washed 3 times with water, dried over sodium sulfate, filtered, concentrated to a residue, and chromatographed on silica gel (methylene chloride/hexane), to yield 0.13 g of (II). M.S.: M+=296; NMR: consistent.

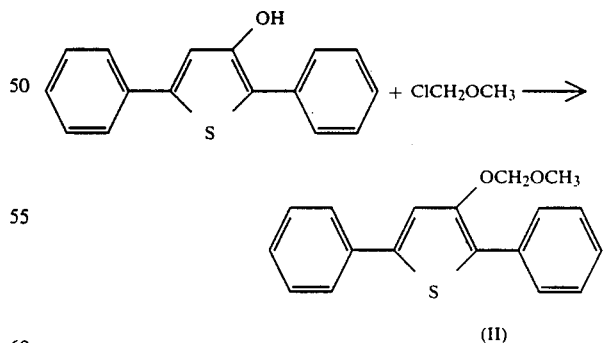

EXAMPLE 4

3-Hydroxy-2,4,5-triphenylthiophene

To an ice cooled, stirred solution of dibenzyl sulfide (2.14 g, 0.01 m) in dried N,N-dimethylformamide was added sodium hydride (0.88 g, 0.022 mmol of a 60% suspension in mineral oil). The mixture was gradually heated to 60° C. (bath temperature), kept 2 hours and allowed to cool. Methyl benzoylformate (1.42 ml, 0.01 mmol) was then added and the mixture heated at 60° C. for 1 hour, cooled, added to a stirred ice-dilute hydrochloric acid-ether mixture, separated, the aqueous layer re-extracted 1 time with ether, and the combined organic layer washed 2 times with water, dried over sodium sulfate, filtered and concentrated to a residue. Chromatography on silica gel (1 time flush with 10% ethyl acetate/hexane followed by a careful chromatography with a methylene chloride/hexane mixture) yielded 50 mg. of product compound as a pale yellow-white crystalline material. M.S.: M+ =328; NMR: consistent, identical to the nmr spectrum of material prepared from α-phenylcinnamic acid and α-mercaptophenylacetic acid via Michael addition and ring closure.

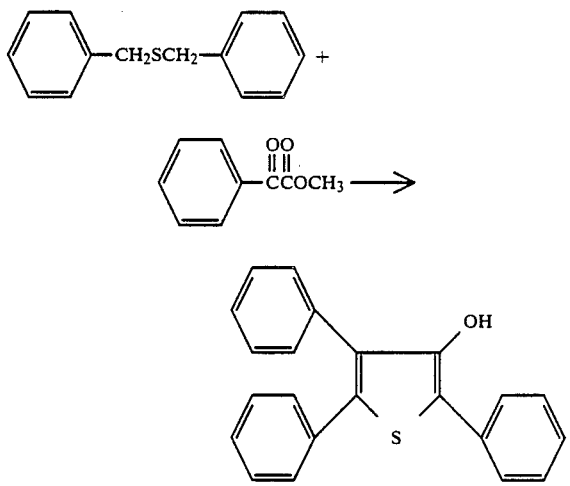

EXAMPLE 5

3-Acetoxy-4-phenylthiophene

Atropic acid (149 mg, 1.10 mmol) and mercaptoacetic acid (80 μl, 106 mg, 1.15 mmol) were combined and stirred 18 hours at 130° C. under a nitrogen atmosphere. The resulting crude Michael addition product was dissolved in acetic anhydride (2.4 mL, 2.6 g, 25 mmol) and sodium acetate (115 mg, 1.4 mmol) was added. The reaction was warmed in an oil bath, increasing the temperature to 150° C. over 1 hour. The mixture was maintained at that temperature for 2.5 hours, then cooled to 25° C. and evaporated. The residue was dissolved in 3.0 mL of dioxane and DDQ (200 mg, 0.88 mmol) was added in portions over 10 minutes. The reaction was stirred 1 hour at 25° C., then for 0.5 hour at 50°–55° C. The mixture was allowed to stand at room temperature overnight, diluted with 3 mL of dichloromethane, and filtered. The precipitate was rinsed with an additional 3 mL of dichloromethane. The solution was evaporated, taken up in 25 mL of ethyl acetate, and washed with 2×15 mL of saturated aqueous sodium bicarbonate followed by 15 mL of saturated aqueous sodium chloride. The residue was dried over sodium sulfate, filtered, and evaporated. The residue was dissolved in a mixture of ethyl acetate and dichloromethane and evaporated onto 1.5 g of silica gel. Flash column chromatography on 5 g of silica gel eluted with 4% ethyl acetate in hexane gave 84 mg (44% yield) of 3-acetoxy 4-phenylthiophene as an almost colorless oil. A similarly prepared sample was further purified by bulb-to-bulb distillation, bp 85°–90° C. (0.2 mm).

EXAMPLE 6

3-Hydroxy-2,5-diphenylthiophene

Potassium tert-butoxide (1.48 g, 13.2 mmol) was dissolved in 20 mL of THF. A solution of ethyl Z-3-(benzylthio)-3-phenyl-2-propenoate (1.25 g, 4.39 mmol) in 5.0 mL of THF was added over 5 minutes, with an additional 2×2.0 mL of THF then used to rinse the starting material into the reaction. The reaction was stirred for 20 minutes at 25° C., then quenched by dropwise addition of 1.0 mL of glacial acetic acid. The mixture was poured into 100 mL of ethyl acetate and washed with 40 mL of saturated aqueous sodium chloride, 10 mL of 2N aqueous hydrochloric acid, and 50 mL of saturated aqueous sodium chloride. The solution was dried over sodium sulfate, decanted, and evaporated. The residue was dissolved in dichloromethane and evaporated onto 6 g of silica gel. Flash column chromatography on 30 g of silica gel eluted with 1 L of 7% ethyl acetate in hexane gave 0.91 g of fluffy white crystals containing a trace of yellow color. Recrystallization from a solution of 10 mL of hexane and 4–5 mL of toluene yielded 0.75 g (68% yield) of 3 hydroxy 2,5-diphenylthiophene, m.p. 118°–120° C.

EXAMPLE 7

3-Hydroxy-2-(4'-methoxyphenyl-5-phenylthiophene

Step A: Preparation of Methyl Z-3-(4'-methoxybenzylthio) 3-phenyl-2-propenoate

Z-3-(4'-Methoxybenzylthio)-3-phenyl-2-propenoic acid (5.46 g, 18.2 mmol) was suspended in 22 mL of dry acetonitrile. Addition of DBU (3.30 mL, 22.1 mmol) gave a clear yellow solution. The mixture was stirred in an ice bath and iodomethane (1.32, 21.2 mmol) was then added over 5 minutes. After an additional 15 minutes, the ice bath was removed and the solution was stirred for 1.25 hours. The reaction was poured into 100 mL of ethyl acetate and washed with 75 mL of water, 2×25 mL of 2N aqueous hydrochloric acid, 2×25 mL of saturated aqueous sodium bicarbonate, and 25 mL of saturated aqueous sodium chloride. The ethyl acetate solution was dried over sodium sulfate, decanted, and evaporated to give 4.53 g of crude methyl Z-3 (4'-methoxybenzylthio)-3-phenyl-2-propenoate as pale yellow crystals.

Step B: Preparation of 3-Hydroxy-2-(4'-methoxyphenyl)-5 -phenylthiophene

Potassium tert-butoxide (2.11 g, 18.8 mmol) was dissolved in 30 mL of THF at 25° C. A solution of crude methyl Z-3-(4'-methoxybenzylthio)-3-phenyl-2-propenoate (2.00 g, 6.36 mmol) in 10 mL of THF was added over 5–10 minutes. An additional 2×2 mL of THF was used to rinse the starting material into the reaction. After stirring an additional 1 hour at 25° C., the reaction was quenched with 1.5 mL of glacial acetic acid and poured into 100 mL of ethyl acetate. After washing successively with 50 mL of saturated aqueous sodium chloride, 15 mL of 2N aq. hydrochloric acid, and 50 mL of saturated aq. sodium chloride, the solution was dried over sodium sulfate, decanted, and evaporated. The residue was dissolved in dichloromethane and evaporated onto 10 g of silica gel. Flash column chromatography on 60 g of silica gel eluted with 1 L of 10% ethyl acete in hexane followed by 500 mL of 12% ethyl acetate in hexane gave 3-hydroxy-2-(4'-methoxyphenyl)-5-phenylthiophene as 0.35 g of off-white crystals.

EXAMPLE 8

3-Acetoxy-2-(4'-methoxyphenyl)-5-phenylthiophene

3-Hydroxy-2-(4'-methoxyphenyl)-5-phenylthiophene (200 mg, 0.71 mmol) was dissolved in 2.0 mL of pyridine and treated with acetic anhydride (0.50 mL, 5.3 mmol). The solution was stirred 4 hours at 25° C., and then most of the acetic anhydride and pyridine were removed on a rotary evaporator at reduced pressure. The residue was dissolved in 40 mL of ethyl acetate and washed with 2×15 mL of 2N aqueous hydrochloric acid, 15 mL of saturated aqueous sodium bicarbonate, and 15 mL of saturated aqueous sodium chloride. The solution was dried over sodium sulfate, decanted, and evaporated. The residual oil (224 mg) began to crystallize upon standing overnight. This was combined with other material prepared by the same method and recrystallized twice from 3–4 mL of 7% ethyl acetate in hexane to give 3-acetoxy-2-(4'-methoxyphenyl)-5-phenylthiophene as very pale pink needles, m.p. 81°–82° C.

EXAMPLE 9

3-Hydroxy-2-(3'-pyridyl-5-phenylthiophene

Step A: Preparation of Ethyl 3-(3'-pyridylmethylthio)-3-phenyl-2-propenoate

Ethyl phenylpropiolate (1.30 mL, 1.37 g, 7.86 mmol) and 3-pyridinemethanethiol (1.00 g, 7.99 mmol) were combined and cooled in an ice bath. Piperidin-e (50 μL, 43 mg, 0.51 mmol) was added dropwise over 10 minutes, giving an exothermic reaction. After an additional 10 minutes, the ice bath was removed and the reaction was allowed to stand overnight. The reaction was then heated to 100° C. for 1 hour. The crude ethyl 3-(3'-pyridylmethylthio)-3-phenyl-2-propenoate, obtained as a mixture of Z-and E-isomers, was used directly in the cyclization.

Step B: Preparation of 3-Hydroxy 2-(3'-pyridyl)-5-phenylthiophene

The crude Michael addition product was dissolved in 5.0 mL of THF and added dropwise over 5–10 minutes to an ice-cooled solution of potassium tert-butoxide (2.65 g, 23.7 mmol) in 25 mL of THF. An additional 2×3 mL of THF was used to rinse the ester starting material into the reaction. The ice bath was removed and the reaction was stirred for 25 minutes, then cooled in an ice bath and quenched by addition of 11.9 mL of 2.0 N aqueous hydrochloric acid. The reaction was partitioned between 50 mL of saturated aqueous sodium chloride and 50 mL of dichloromethane. The organic layer was washed with and additional 50 mL of saturated aqueous sodium chloride and dried over sodium sulfate. The aqueous layers were extracted in succession with 2×50 mL of saturated aqueous sodium chloride and the organic layers were dried over sodium sulfate. The organic layers were decanted and evaporated to give a sticky crystalline residue. Stirring with 10 mL of ethyl acetate, filtration, and washing with 5 mL of ethyl acetate left 1.25 g of pale yellow crystals. Recrystallization from a boiling mixture of 20 mL of ethyl acetate and 10 mL of ethanol allowed to cool to 25° C. gave 3-hydroxy-2-(3'-pyridyl)-5-phenylthiophene as 675 mg of pale yellow crystals, m.p. 202°–204° C.

EXAMPLE 10

3-Acetoxy-2-(3'-pyridyl)-5-phenylthiophene

3-Hydroxy 2-(3'-pyridyl)-5-phenylthiophene (115 mg, 0.454 mmol) was suspended in 2.0 mL of acetonitrile and triethylamine (130 μL, 94 mg, 0.93 mmol) was added followed by dimethylaminopyridine (3 mg, 0.02 mmol). The hydroxy compound still remained largely undissolved, but the addition of acetic anhydride (130 μL, 141 mg, 1.38 mmol) gave a solution which was allowed to stand overnight. The reaction mixture was then evaporated and the residue was purified by flash column chromatography on 5 g of silica gel eluted with 1mL ethyl acetate in hexane, giving 132 mg of pale orange crystals. Recrystallization from a solution of 1 mL of hexane and 0.5–0.75 mL of toluene at 5° C., with slow cooling to 0° C., gave 96 mg of 3-acetoxy-2-(3'-pyridyl)5-phenylthiophene, m.p. 76°–77° C.

EXAMPLE 11

3-Hydroxy-5-(2-methylphenyl)-2-phenylthiophene

A solution of methyl Z-3-(2'methylphenyl)-3-benzylthio-2-propenoate (575 mg, 1.93 mmol) in 6.0 mL of THF was added through a double ended needle to a solution of potassium tert-butoxide (650 mg, 5.79 mmol) in 8.0 mL of THF at ambient temperature. An additional 2×1 mL of THF was used to rinse the ester into the reaction. The bright orange-green reaction as stirred 20 minutes at 25° C., then cooled in an ice bath and quenched by the addition of 3.5 mL of 2.0 N aqueous hydrochloric acid. The reaction was poured into 25 mL of saturated aqueous sodium chloride and extracted with 2×25 mL of ethyl acetate. The ethyl acetate layers were washed in succession with 25 mL of saturated aqueous sodium chloride, combined, dried over sodium sulfate, decanted, and evaporated. Flash column chromatography on 15 g of silica gel eluted with 500 mL of 3% ethyl acetate in hexane followed by 200 mL of 6% ethyl acetate in hexane gave 3-hydroxy-5-(2'-methylphenyl)-2-phenylthiophene as 385 mg of pale yellow viscous oil (75% yield). The product could be distilled bulb to bulb, bp (0.4 mm) 140°–150° C.

EXAMPLE 12

3-Hydroxy-2-(2'-methylphenyl)-5-phenylthiophene

A solution of methyl Z-3-(2'-methylbenzylthio)-3-phenyl-2-propenoate (900 mg, 3.02 mmol) in THF (8 mL) was added dropwise through a double-ended needle to a solution of potassium tert-butoxide (1.02 g, 9.09 mmol) in THF (12 mL). An additional 2 mL of THF was used to rinse the ester into the reaction. The reaction was stirred 30 minutes at 25° C., then cooled in an ice bath and quenched by the addition of 7.0 mL of 2.0 N aqueous hydrochloric acid. The reaction was poured into 50 mL of saturated aqueous sodium chloride solution and extracted with 2×50 mL of ethyl acetate. The ethyl acetate layers were washed in succession with 50 mL of saturated aqueous sodium chloride, dried over sodium sulfate, filtered, and evaporated. Flash column chromatography on 45 g of silica gel, eluting with 500 mL of 4% ethyl acetate in hexane followed by 500 mL of 6% ethyl acetate in hexane, gave 3-hydroxy-2-(2'-methyl phenyl) 5-phenylthiophene as an oil weighing 421 mg. The product could be distilled bulb-to-bulb, bp (0.4 mm) 140°–150° C.

EXAMPLE 13

3-Acetoxy-2-(2'-methylphenyl)-5-phenylthiophene

3-Hydroxy-2-(2-methylphenyl)-5-phenylthiophene (537 mg, 2.02 mmol) was dissolved in acetonitrile (4.0 mL), and 4-dimethylaminopyridine (15 mg, 0.12 mmol) and triethylamine (0.65 mL, 470 mg, 6.9 mmol) were added followed by acetic anhydride (0.65 mL, 700 mg, 6.9 mmol). The reaction was stirred overnight at 25° C. The reaction mixture was evaporated and the residue was chromatographed on 30 g of silica gel eluting with 700 mL of 15% ethyl acetate in hexane. 3-Acetoxy-2-(2'-methylphenyl)-5-phenylthiophene was isolated as 370 mg of viscous oil. The product could be distilled bulb-to-bulb, bp (0.4 mm) 140°-150° C.

EXAMPLE 14

3-Acetoxy-2-(4-methoxyphenyl)-4,5,6,7-tetrahydrobenzo [b]thiophene

Step 1:

Ethyl 2,2-bis-(4-methoxyphenyl)methylthiocyclohexane carboxylate

A solution of 1.70 g (10 mmol) of ethyl 2-oxocyclohexanecarboxylate and 3.38 g (22 mmol) of p-methoxybenzylmercaptan in 20 mL toluene was heated to reflux under nitrogen. Then 0.10 g (0.48 mmol) of p-toluenesulfonic acid monohydrate was added and the solution was heated at reflux with a Dean-Stark trap for 4 hours. The solution was partitioned between NaHCO$_3$ and ether and the ether layer was washed with NaHCO$_3$ and brine and dried over MgSO$_4$. The solution was concentrated and the oily residue was chromatographed on silica gel (10% ethyl acetate-hexane) to afford 2.82 g (62%) of a clear oil NMR (CDCl$_3$,(CH$_3$)$_4$Si) $\delta$1.31 (3H, t, J=7Hz), 1.6-2.1 (6H, m), 2.3-2.5 (2H, m), 2.93 (1H, t, J=6Hz), 3.78-3.95 (10H, m) 4.20 (2H, g, J=7Hz), 6.82, (2H, AB), 6.84 (2H, AB), 7.25 (2H, AB), 7.27 (2H, AB); Mass Spectrum: m/e 452 (M+).

Step 2:

3-Acetoxy-2-(4-methoxyphenyl)-4,5,6,7-tetrahydrobenzo [b]thiophene

A solution of 1.5 mL (10.7 mmol) of diisopropylamine in 10 mL of dry tetrahydrofuran was cooled to −78° under nitrogen. To this was added 4 mL of 2.5M n-butyllithium (in hexane) and after 15 minutes, a solution of 1.36 g (3 mmol) of ethyl 2,2-bis-(4-methoxyphenyl)methylthiocyclohexanecarboxylate in 5 mL of dry tetrahydrofuran was added and the solution was stirred under N$_2$ for 2 hours. Then 1.5 mL (15 mmol) of acetic anhydride was added and the solution was stirred at room temperature for 1 hour. The solution was partitioned between ether and NaHCO$_3$ and the ether layer was washed with NaHCO$_3$, then brine, and dried over MgSO$_4$. The solution was concentrated and the residue chromatographed on silica gel (20% ethyl acetate-hexane) to afford a colorless oil. This was crystallized from ethyl acetate-hexane to afford 0.394 g (47%) of title compound as a white crystalline solid, m.p. 81° C. NMR (CDCl$_3$, (CH$_3$)$_4$Si) $\delta$1.81 (4H, m), 2.25 (3H, s, CH$_3$CO), 2.35 (2H, t, J=6Hz), 2.71 (2H, t J=6Hz), 3.80 (3H, s, OCH$_3$), 6.90 (2H, AB), 7.39 (2H, AB).

EXAMPLE 15

Step 1:

Methyl 3-(4'-methoxyphenyl)methylthioindene-1H-2-carboxylate

A solution of 3.80 g (20 mmol) of methyl 1-oxoindane-2-carboxylate and 5.90 g (22 mmol) of diphenyl chlorophosphate in 100 mL of dry tetrahydrofuran was cooled to 0° under nitrogen. Then 3.0 mL (22 mmol) of triethylamine was added and the solution was stirred at 0° for 1 hour. A solution of 3.39 g (22 mmol) of 4-methoxybenzyl mercaptan in 20 mL of dry tetrahydrofuran was added and after 10 minutes, 3.3 mL (24 mmol) of triethylamine was added by syringe. The mixture was stirred at room temperature for 2 hours, then was partitioned between ether and water. The ether layer was washed with NaHCO$_3$ and brine, dried over MgSO$_4$, and concentrated. The residue was chromatographed on silica gel (10% ethyl acetatehexane) hexane) to afford 5.96 g (85%) of a colorless oil. NMR (CDCl$_3$, (CH$_3$)$_4$Si) $\delta$3.72 (2H, s, SCH$_2$Ar), 3.77 (3H, s, COOCH$_3$), 3.88 (3H, s, ArOCH$_3$), 4.34 (2H, s, CH$_2$), 6.78 (2H, AB), 7.21 (2H, AB), 7.39 (2H, m), 7.48 (1H, m), 7.74 (1H, m); Mass Spectrum: m/e 336 (M+).

Step 2:

-Acetoxy-2-(4'-methoxyphenyl)-4H-indeno[1,2-b]thiophene

A solution of 3.0 mL (21 4 mmol) of diisopropylamine in 20 mL of dry tetrahydrofuran was cooled to −78° under nitrogen. To this was added 8 mL of 2.5M n-butyllithium (in hexane) and after 15 minutes, a solution of 3.26 g (10 mmol) of methyl 3-(4'-methoxyphenyl)-methylthio-1H-indene 2-carboxylate was added and the solution was stirred at −78°. After 2 hours, 3 mL (30 mmol) of acetic anhydride was added and the solution was stirred at room temperature for 1 hour. The solution was partitioned between ether and water and the ether layer was washed with NaHCO$_3$ and brine, dried over MgSO$_4$, and concentrated. The residue was chromatographed on silica gel (20% ethyl acetate-hexane) and the product was crystallized from ethyl acetate-hexane to afford 1.19 g (35% of the title compound as fine white needles, m.p. 129° C. NMR (CDCl$_3$, (CH$_3$)$_4$Si) $\delta$ 2.35 (3H, s, CH$_3$CO), 3.74 (2H, s, CH$_2$), 3.95 (3H, s, ArOCH$_3$), 6.95 (2H, AB), 7.1–7.4 (2H, m), 7.44 (2H, AB), 7.51 (2H, m).

EXAMPLE 16

Step 1:

Methyl 1-(4'-methoxyphenyl)methylthio-4,5 dihydro-3H-benzocycloheptene-2-carboxylate A suspension of 2.18 g (10.0 mmol) of methyl 1-oxo-2,3,4,5 tetrahydro-1H-benzocycloheptene-2-carboxylate and 1.24 g (11.0 mmol) of potassium t-butoxide in 50 mL of tetrahydrofuran was heated at reflux under nitrogen until the solid dissolved. Then 2.86 g (11.0 mmol) of diphenyl chlorophosphate was added and heating was continued. After 30 minutes, a solution of 1.69 g (11.0 mmol) of 4-methoxybenzyl mercaptan in 10 mL of dry tetrahydrofuran was added, followed by three portions (1.24 g (11.0 mmol) total) of potassium t-butoxide. The solution was heated at reflux for 4 hours, then cooled and partitioned between ether and water. The ether layer was washed with NaHCO$_3$, then brine, dried over MgSO$_4$, and concentrated.

The oily residue was chromatographed on silica gel (10% ethyl acetate hexane) to afford an oil that afforded 2.73 g (77%) of title compound as white crystals, m.p. 79°-81° C. NMR (CDCl$_3$, (Ch$_3$)$_4$Si) $\delta$1.90–2.10 (6H, m), 3.55 (2H, s, SCH$_2$Ar), 3.82 (3H, s, OCH$_3$), 3.90 (3H, s, OCH$_3$) 6.65 (2H, AB), 6.75 (2H, AB), 7.12 (1H, d of d, J=7, 1.5 Hz), 7.28 (1H, t of d, J=7, 1.5 Hz), 7.35 (1H, t of d, J=7, 1.5 Hz), 7.56 (1H, d of d, J=7, 1 5 Hz).

Step 2:

3-Acetoxy-5,6-dihydro-2-(4-methoxyphenyl) 4H-benzo-[6,7]cyclohepta[1,2-b]thiophene A solution of 1.0 mL (7.1 mmol) of diisopropylamine in 10 mL of dry tetrahydrofuran was cooled to −78° under nitrogen. To this was added 2 mL of 2.5M n-butyllithium (in hexane) and after 15 minutes, a solution of 0.73 g (2.00 mmol) of methyl 1-(4'-methoxyphenol)-methylthio-4,5-dihydro 3H-benzocycloheptene-2-carboxylate was added and the solution was stirred at −78°. After 2 hours, 1 mL (10 mmol) of acetic anhydride was added and the solution was stirred at room temperature for 1 hour. The solution was partitioned between ether and water and the ether layer was washed with NaHCO$_3$ and brine, dried over MgSO$_4$, and concentrated. The residue was chromatographed on silica gel (20% ethyl acetatehexane) and that product was crystallized from ethyl acetate-hexane to afford 0.263 g (36%) of the title compound as fine white needles, m.p. 154° C. NMR (CDCl$_3$, (CH$_3$)$_4$Si) δ 2.10–2.25 (4H, m), 2.30 (3H, s, CH$_3$CO), 2.50 (2H, t, J=7.5Hz), 2.76 (2H, t, J=7.5Hz), 3.95 (3H, s, OCH$_3$), 6.92 (2H, AB), 7.2–7.3 (4H, m), 7.49 (2H, AB).

EXAMPLE 17

Assays of biological activity

Two screening methods were employed for the purposes of evaluating the biological activities of the compounds of the present invention. The PMN5LO assay is a direct measure of the capacity to inhibit 5-lipoxygenase. The second protocol, RSVM-CO, is a method of determining inhibition of cyclooxygenase enzyme activity and as such it serves as a negative control.

The steps for conducting each of these two biological assays is as follows:

A. PMN5LO Assay Protocol

Elicition of Rat Peritoneal polymorphonuclear leukoytes (PMN)

Male Sprague-Dawley rats (about 350 grams) were injected intraperitoneally the day before use with 8 ml of 12% sodium caseinate. The next day the animals were killed by CO$_2$ asphyxiation and the peritoneal cavity lavaged twice with 20 ml of Hanks balanced salts containing 15 mM HEPES (pH 7.4), 1.4 mM Ca++ and 0.7 mM Mg++ (Hepes-Hanks). The suspensions were filtered through plastic mesh and centrifuged at 260 mg for 5 minutes. The cells were resuspended in 50 ml Hepes-Hanks and recentrifuged. The PMN pellets were combined and suspended at 1.25×10$^7$ cells/ml.

Incubations

The cell suspension was then diluted 1:10, preincubated 5 minutes at 37° C. and distributed in 200 μl aliquots in the wells of 96 well microtiter plates. The wells had previously received samples of the compounds of the present invention, controls, etc., in 25 μl of 0.001% fatty acidfree BSA in Hepes-Hanks. The plates were incubated 2 minutes at 37° C. and then the cells were stimulated to produce LTB$_4$ by the addition of 25 μl of 100 μM calcium ionophore, designated A23187. After 4 minutes at 37° C. the plates were frozen in dry ice.

Radioimmunoassay (RIA) of LTB$_4$

The frozen plates were thawed to 4° C. and 25 μl aliquots removed to V well plates. Antibody to LTB$_4$ (50 μl) was added and, after 15 minutes at room temperature, 50 μl of $^3$H-LTB$_4$ was added and the plates were stored overnight at 4° C. to allow equilibration. The next day the "free" 3H-LTB$_4$ was removed by adsorption to dextran coated charcoal [90 μl per well of a 4% charcoal suspension with 0.25% Dextran T-70 in 10 mM potassium phosphate (pH 7.3) containing 1mM EDTA and 0.25 mM thimerasol] during a 10 minute ice temperature incubation. The charcoal was removed by a 10 minute centrifugation at 200 sg. Aliquots of the supernatant were counted in a Packard 460, analyzed in a Masscomp computer and the data drawn up as % inhibition of LTB$_4$ production.

B. Ram Seminal Vesicle Microsomal Cyclooxygenase (RSVM-CO) Assay Protocol

Enzyme Preparation

Ram seminal vesicular glands were trimmed of fat, 50 grams diced into 250 mls ice cold 0.1 M potassium phosphate (pH 7.6) buffer and homogenized using a Brinkman Polytron. The suspension was centrifuged 10 minutes at 10K mg (4° C.) and the supernatant filtered through two cheesecloth layers. The filtrate was centrifuged 160 minutes at 105K xg, the supernatant thereof discarded, and the pellet surface rinsed with a small volume of buffer. The pellets were combined in a small volume, briefly homogenized with the Polytron and frozen in 0.5 ml aliquots at −80° C. The protein concentration was about 50 mg/ml.

Incubation

The thawed enzyme was diluted 1:63 with 0.125 M Na EDTA (pH 8.0) containing 50 μg/ml BSA. A substrate-cofactor premix was prepared with 66 μM $^{14}$C-arachidonic acid (about 20K cpm/12.5 μl) in 500 μl 0.125 M Na EDTA (pH 8.0) plus 10 μl 50 mM hydroquinone and 10 μl 200 mM glutathione. To each sample well in the 96 well plate, agents dissolved in 0.5 μ DMSO were added, followed by 12.5 μl of the diluted enzyme. After a 4 minute preincubation at room temperature, 12.5 μl of the substrate-cofactor mix was added to start the reaction. The reaction was terminated after 20 minutes at room temperature by adding 25 μl of methanol containing 200 μg PGE2 and 400 μg AA per ml.

Assay

The entire reaction mixture was spotted onto a preadsorbent silica gel GF thin layer plate and, after air drying 45 minutes, developed 12 cm in ethyl acetate:glacial acetic acid (99:1).

The developed lanes were scanned for the distribution of radiolabel using a Bioscan Imaging Detector and the integrated peaks compared to standards and controls yielding % inhibition.

The results are tabulated below.

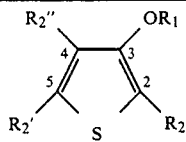

| Cmpd | R₁ | R₂ | R₂' | R₂'' | μg/ml---% inhibition[1] PMN5LO | RSVM-CO |
|---|---|---|---|---|---|---|
| 1. | acetyl | H | phenyl | H | 1 → 18<br>0.33 → 19<br>0.11 → 1<br>0.037 → 0<br>0.012 → 5 | |
| 2. | H | phenyl | phenyl | phenyl | 10 → 95<br>1 → 53<br>0.3 → 0<br>0.11 → 0<br>0.037 → 14<br>0.012 → 22<br>IC₅₀[2] ~ 3000 nM | 10 → 23 |
| 3. | acetyl | phenyl | phenyl | H | 0.05 → 100<br>0.037 → 57<br>0.012 → 27<br>IC₅₀ = 88 nM<br>0.11 → 100<br>0.037 → 56<br>0.012 → 38<br>IC₅₀ = 74 nM | 10 → 29<br>1 → 8<br>0.1 → 13<br>0.01 → 13 |
| 4. | H | phenyl | phenyl | H | 1 → 99<br>0.33 → 98<br>0.11 → 97<br>0.037 → 69<br>0.012 → 17<br>IC₅₀ = 110 nM<br>1 → 88<br>0.33 → 85<br>0.11 → 70<br>0.037 → 29<br>0.012 → 11 | 10 → 92<br>2 → 46<br>1 → 6<br>0.4 → 18<br>0.1 → 24 |
| 5. | $-\overset{O}{\underset{\parallel}{C}}-CH_3$ | phenyl | (3-CF₃-phenyl) | H | 1 → 38 | |
| 6. | $-\overset{O}{\underset{\parallel}{C}}-CH_2CH_3$ | phenyl | (3-CF₃-phenyl) | H | 1 → 22 | |
| 7. | $-\overset{O}{\underset{\parallel}{C}}-CH_3$ | phenyl | phenyl | phenyl | 1 → 10<br>0.33 → 8<br>0.11 → 3<br>0.037 → 23<br>0.012 → 26<br><br>1 → 0<br>0.33 → 19<br>0.11 → 16<br>0.037 → 7<br>0.012 → 6<br>IC₅₀ > 3000 nM | 5 → 76<br>1 → 12<br>0.1 → 0<br>0.01 → 0 |
| 8. | $-\overset{O}{\underset{\parallel}{C}}-CH_3$ | phenyl | phenyl | phenyl | 1 → 18 | |
| 9. | $-\overset{O}{\underset{\parallel}{C}}-CH_3$ | methyl | phenyl | phenyl | 1 → 13 | |

-continued

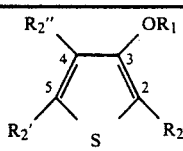

| Cmpd | $R_1$ | $R_2$ | $R_2'$ | $R_2''$ | PMN5LO (μg/ml---% inhibition[1]) | RSVM-CO |
|---|---|---|---|---|---|---|
| 10. | $-\overset{O}{\underset{\|}{C}}-CH_2-OCH_3$ | phenyl | phenyl | H | 1 → 58<br>0.33 → 100<br>0.11 → 73<br>0.037 → 28<br>$IC_{50}$ = 200 nM<br>1 → 100<br>0.33 → 100<br>0.11 → 100<br>0.037 → 51<br>0.012 → 0<br>$IC_{50}$ = 110 nM | 0.1 → 60 |
| 11. | $-\overset{O}{\underset{\|}{C}}-CH_3$ | phenyl | thienyl | H | 1 → 74<br>0.33 → 52<br>0.11 → 51<br>0.037 → 22<br>0.012 → 0<br>1 → 100<br>0.33 → 100<br>0.11 → 100<br>0.037 → 51<br>0.012 → 46 | 1 → 0<br>0.1 → 0<br>0.01 → 0 |
| 12. | $CH_2OCH_3$ | phenyl | phenyl | H | 1 → 32<br>0.33 → 74<br>0.11 → 31<br>0.037 → 0<br>0.012 → 34<br>$IC_{50}$ = 580 nM<br>1 → 100<br>0.33 → 84<br>0.11 → 40<br>0.037 → 22<br>0.012 → 11<br>$IC_{50}$ = 350 nM | 1 → 100<br>0.1 → 0<br>0.01 → 28 |
| 13. | (cyclohexyl-fused thiophene with OAc and p-methoxyphenyl substituents) | | | | 1 → 100<br>0.33 → 85<br>0.11 → 21<br>0.037 → 20<br>0.012 → 4<br>$IC_{50}$ = 650 nM<br>1 → 97<br>0.33 → 88<br>0.11 → 51<br>0.037 → 6<br>0.012 → 20<br>$IC_{50}$ = 380 nM | 1 → 11<br>0.1 → 100 |
| 14. | Acetyl | p-methoxy phenyl | $R_2'$ = phenyl | $R_2''$ = H | 1 → 100<br>0.33 → 100<br>0.11 → 91<br>0.037 → 70<br>0.012 → 24<br>$IC_{50}$ = 80 nM<br>1 → 80<br>0.33 → 85<br>0.11 → 46<br>0.037 → 16<br>0.012 → 12 | 0.1 → 0 |
| 15. | Acetyl | H | H | phenyl | 1 → 10<br>0.33 → 0<br>0.11 → 0<br>0.037 → 0<br>0.012 → 9 | 1 → 0<br>0.1 → 0 |
| 16. | Acetyl | 3-pyridyl | $R_2'$ = phenyl | $R_2''$ = H | 1 → 100<br>0.33 → 94<br>0.11 → 63<br>0.037 → 22<br>0.012 → 15<br>$IC_{50}$ = 230 nM | 1 → 0<br>0.1 → 0 |

-continued

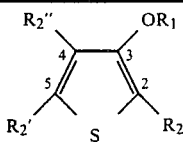

| Cmpd | R₁ | R₂ | R₂' | R₂'' | μg/ml---% inhibition[1] | |
|---|---|---|---|---|---|---|
| | | | | | PMN5LO | RSVM-CO |
| | | | | | 1 → 88 | |
| | | | | | 0.33 → 84 | |
| | | | | | 0.11 → 26 | |
| | | | | | 0.037 → 1 | |
| | | | | | 0.012 → 0 | |
| 17. | \[structure: indane-fused thiophene with OAc and 4-methoxyphenyl\] | | | | 1 → 54 | |
| | | | | | 0.33 → 20 | |
| | | | | | 0.11 → 0 | |
| | | | | | 0.037 → 10 | |
| | | | | | 0.012 → 0 | |
| | | | | | IC₅₀ = 2500 nM | |
| | | | | | 1 → 18 | |
| | | | | | 0.33 → 0 | |
| | | | | | 0.11 → 25 | |
| | | | | | 0.037 → 26 | |
| | | | | | 0.012 → 0 | |
| | | | | | 1 → 100 | |
| | | | | | 0.33 → 83 | |
| | | | | | 0.11 → 23 | |
| | | | | | 0.37 → 42 | |
| | | | | | 0.012 → 36 | |
| 18. | H | phenyl | 2-methyl phenyl | H | 1 → 96 | |
| | | | | | 0.33 → 100 | |
| | | | | | 0.11 → 96 | |
| | | | | | 0.037 → 46 | |
| | | | | | 0.012 → 20 | |
| | | | | | IC₅₀ = 120 nM | |
| 19. | CH₃ | phenyl | phenyl | H | 1 → 0 | |
| | | | | | 0.33 → 0 | |
| | | | | | 0.11 → 0 | |
| | | | | | 0.037 → 0 | |
| | | | | | 0.012 → 0 | |
| 20. | \[structure: benzocycloheptane-fused thiophene with OAc and 3-methoxyphenyl\] | | | | IC₅₀ >> 3000 nM | |
| 21. | \[structure: diphenyl thiophene with OAc and CH₃\] | | | | 1 → 79 | |
| | | | | | 0.33 → 34 | |
| | | | | | 0.11 → 17 | |
| | | | | | 0.037 → 15 | |
| | | | | | 0.012 → 15 | |
| 22. | H | 3-pyridyl | phenyl | H | 1 → 87 | |
| | | | | | 0.33 → 81 | |
| | | | | | 0.11 → 45 | |
| | | | | | 0.037 → 19 | |
| | | | | | 0.012 → 14 | |
| 23. | \[structure: 2,5-diphenyl thiophene\] | | | | 1 → 38 | |
| | | | | | 0.33 → 23 | |
| | | | | | 0.11 → 15 | |
| | | | | | 0.037 → 0 | |
| | | | | | 0.012 → 13 | |
| | | | | | IC₅₀ = 4000 nM | |

-continued

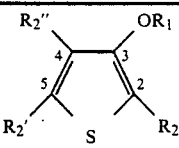

| Cmpd | R₁ | R₂ | R₂' | R₂'' | μg/ml---% inhibition[1] | |
|---|---|---|---|---|---|---|
| | | | | | PMN5LO | RSVM-CO |
| 24. | | 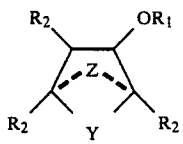 | | | 1 → 33<br>1 → 66<br>0.33 → 53<br>0.11 → 36<br>0.037 → 6<br>0.012 → 25 | |

[1]In each entry, the first number gives the concentration of inhibitor in μg/ml, the second number gives the percent inhibition. Thus, for compound 1, a concentration of 1 μg/ml gives an inhibition of 18% by the assay described in section A of this example.
[2]IC$_{50}$ is the estimated concentration required for 50% inhibition.

While the foregoing specification teaches sthe principles of the present invention, with examples provided for the purpose of illustration, it will be understood that the practice of the invention encompasses all of the usual variations, adaptations, modifications, deletions or additions of procedures and protocols described herein, as come within the scope of the present invention, as exemplified by the following claims.

What is claimed is:

1. A thiophene derivative of the formula:

I or a physiologically acceptable salt thereof, wherein Z represents the number of double bonds in the 5-membered ring and Z=1 or 2; Y is S;

R₁ is
(a) H;

(b)
wherein R₃ is C$_{1-6}$ alkyl, aryloxy, loweralkoxy, lower alkylthio, monoloweralkylamino, diloweralkylamino, loweralkoxy loweralkyl, or carboloweralkoxy loweralkyl;

(c)

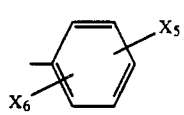

wherein R₄ is naphthyl, anthryl, or substituted phenyl of formula

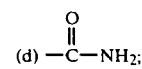

wherein X₅ and X₆ independently are:

(1) Q, where Q is H, C$_{1-6}$ alkyl, fluoro or chloro C$_{1-6}$ alkyl, phenyl or substituted phenyl, or naphthyl;
(2) halo;
(3) C$_{2-6}$ alkynyl;
(4) C$_{2-6}$ alkenyl;
(5) —SQ;
(6) —OQ;
(7) —CHQCOQ¹, wherein Q¹ is any species of Q and can be the same as or different from Q;
(8) —CHQCOOQ¹;
(9) —CH₂SQ or —CHQSQ¹;
(10) —CH₂OQ or —CHQOQ¹;
(11) —COQ;
(12) —COOQ;
(13) —OCOQ;
(14) —CQQ¹;
(15) —NQCOQ¹;
(16) —NQ(OQ¹);
(17) —NQ(SQ¹);
(18) —NQSO₂Q¹;
(19) —SO₂NQQ¹;
(20) —SOQ;
(21) —SO₂Q;
(22) —SO₃Q;
(23) —CN;
(24) —NO₂;
(25) —CONQQ¹;
(26) —NO;
(27) —CSQ;
(28) —CSNQQ¹;
(29) —CF₂SQ;
(30) —CF₂OQ;
(31) —NQCONHQ¹ or NQCONQ¹Q² wherein Q² is any species of Q and Q¹ is any species of Q, and Q² can be the same as or different from Q¹;

(d) —C(O)—NH₂;

(e) —R₃—OR₃;
(f) —R₃—S—R₃; or
(g) QOQ¹; and

R₂ in the 2-position of the thiophene is
(a) R₄; or (b) heteroaryl substituted with $X_5$ and $X_6$ and selected from the group consisting of pyridyl, pyrryl, furyl and thienyl, wherein $X_5$ and $X_6$ are as previously defined; and $R_2$ in the 4- and 5-position of the thiophene forms, a bridged alkylene of between 3 and 10 carbon atoms or a bridged alkylene of between 3 and 10 carbon atoms including a phenyl group fused to an alpha and beta carbon thereof.

2. A thiophene derivative of claim 1, with the structure

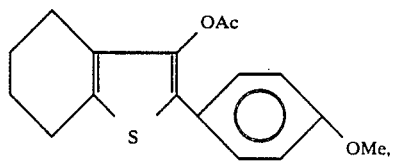

or physiologically acceptable salts thereof.

3. A thiophene derivative of claim 1, with the structure

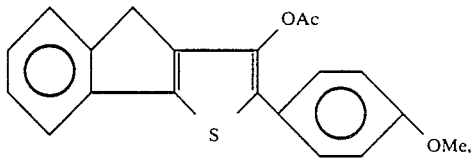

or physiologically acceptable salts thereof.

4. A thiophene derivative of claim 1, with the structure

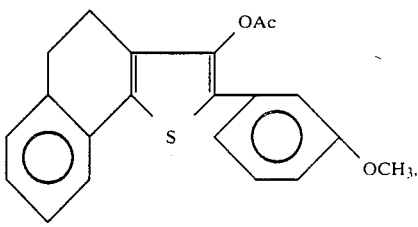

or physiologically acceptable salts thereof.

* * * * *